US010898697B2

(12) United States Patent
Marsico et al.

(10) Patent No.: US 10,898,697 B2
(45) Date of Patent: Jan. 26, 2021

(54) MALE INSERT FOR DRAINING FLUID FROM A PATIENT

(71) Applicant: KIRN MEDICAL DESIGN, LLC, Lexington, KY (US)

(72) Inventors: Ben Marsico, Lexington, KY (US); David A. Atashroo, Stanford, CA (US); David S. Kirn, Lexington, KY (US)

(73) Assignee: KIRN MEDICAL DESIGN, LLC, Lexington, KY (US)

( * ) Notice: Subject to any disclaimer, the term of this patent is extended or adjusted under 35 U.S.C. 154(b) by 477 days.

(21) Appl. No.: 15/725,614

(22) Filed: Oct. 5, 2017

(65) Prior Publication Data

US 2019/0105473 A1    Apr. 11, 2019

(51) Int. Cl.
*A61M 27/00* (2006.01)
*A61M 39/12* (2006.01)
(Continued)

(52) U.S. Cl.
CPC ............ *A61M 27/00* (2013.01); *A61M 1/008* (2013.01); *A61M 1/0072* (2014.02);
(Continued)

(58) Field of Classification Search
CPC ...... A61M 27/00; A61M 39/12; A61M 39/24; A61M 39/26; A61M 1/0072; A61M 1/0086; A61M 1/008; A61M 2039/2426; A61M 39/10; A61M 39/1011; A61M 39/1055; A61M 2039/229; A61M 2039/1088; A61M 2039/2486; A61M 2039/0282; A61M 2039/1027; A61M 2039/1033; A61M 39/165; A61M 25/0014; A61M 2202/08; A61M 2210/04; A61M 2013/00157; A61M 2013/0017; A61M 2013/00174; A61M 1/0088; A61M 1/009; A61M 1/00; A61M 1/0001; A61M 1/0003; A61M 25/00;
(Continued)

(56) References Cited

U.S. PATENT DOCUMENTS 3,810,471 A    5/1974   Truhan
5,370,610 A    12/1994  Reynolds
(Continued)

FOREIGN PATENT DOCUMENTS

WO    2010041084 A1    4/2010

*Primary Examiner* — Ophelia A Hawthorne
*Assistant Examiner* — Heather K Barnwell
(74) *Attorney, Agent, or Firm* — Michael S. Hargis; King & Schickli, PLLC

(57) ABSTRACT

A male insert for draining fluid from a patient is provided. The male insert includes a housing, a valve stem supported by the housing for pivotal movement about an axis from an extended position allowing insertion into the patient to a retracted position preventing re-insertion into the patient, a tube connected to the valve stem and supported by the housing for rotational movement about the axis, the tube and the valve stem forming a contiguous channel through which the fluid drains, a stop preventing rotational movement of the tube in a first position and allowing rotational movement of the tube in a second position, and a locking tab engaging one of the valve stem and the tube when the valve stem is in the retracted position.

27 Claims, 17 Drawing Sheets

(51) Int. Cl.
*A61M 1/00* (2006.01)
*A61M 39/24* (2006.01)
*A61M 39/26* (2006.01)

(52) U.S. Cl.
CPC .......... *A61M 1/0086* (2014.02); *A61M 39/12* (2013.01); *A61M 39/24* (2013.01); *A61M 39/26* (2013.01); *A61M 2039/2426* (2013.01)

(58) Field of Classification Search
CPC ............ A61M 25/0017; A61M 25/002; A61M 25/0111; A61M 25/0113; A61M 27/002; A61M 27/006; A61M 27/008; A61M 2027/004; A61M 39/00; A61M 39/22; A61M 2039/0229; A61M 2039/0276; A61M 2039/0261; A61M 2039/1077; A61M 2039/1083; A61M 2039/1094; F16L 37/00; F16L 27/00; A61B 17/320016; A61B 2017/00792; A61B 2017/00796; A61B 2018/00452; A61B 2018/00458; A61B 2018/00464; A61B 2018/0091; A61F 13/00068; A61F 13/02; A61F 13/0203; A61F 13/0216
See application file for complete search history.

(56) References Cited

U.S. PATENT DOCUMENTS

| | | |
|---|---|---|
| 2005/0234390 A1 | 10/2005 | Buckman et al. |
| 2009/0163893 A1 | 6/2009 | Opie et al. |
| 2010/0100056 A1* | 4/2010 | Cawthon ............. A61M 39/165 604/256 |
| 2010/0286596 A1 | 11/2010 | Hofmann et al. |
| 2011/0170943 A1* | 7/2011 | Su ....................... F16C 11/0619 403/74 |
| 2014/0021714 A1* | 1/2014 | Ueda .................. A61M 39/1011 285/81 |
| 2014/0358095 A1 | 12/2014 | Christensen et al. |
| 2017/0189591 A1* | 7/2017 | Visaria ............... A61M 1/0088 |

* cited by examiner

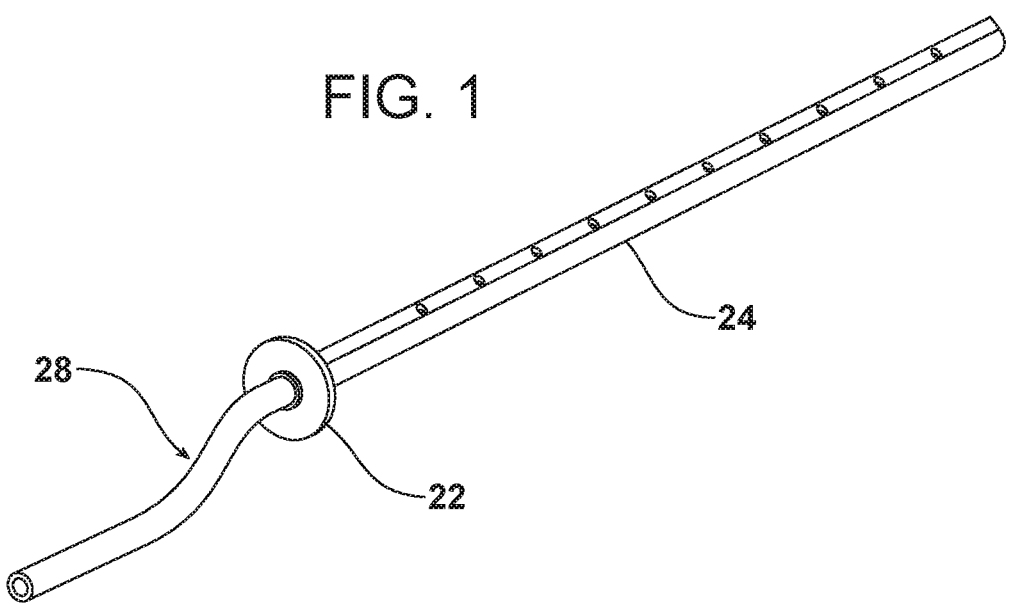
FIG. 1
FIG. 2
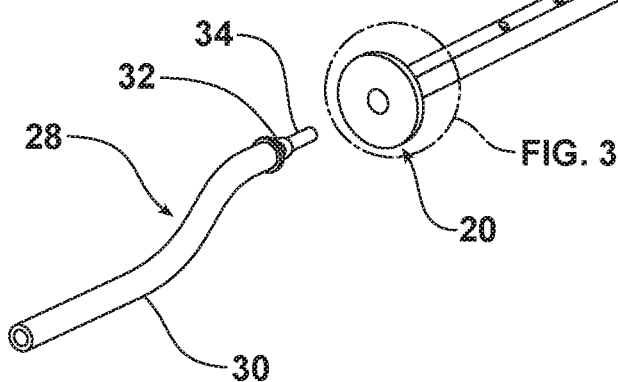
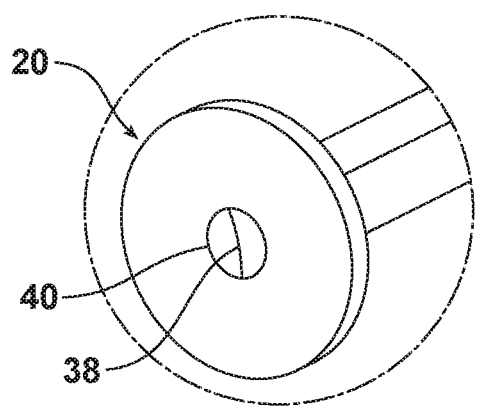
FIG. 3

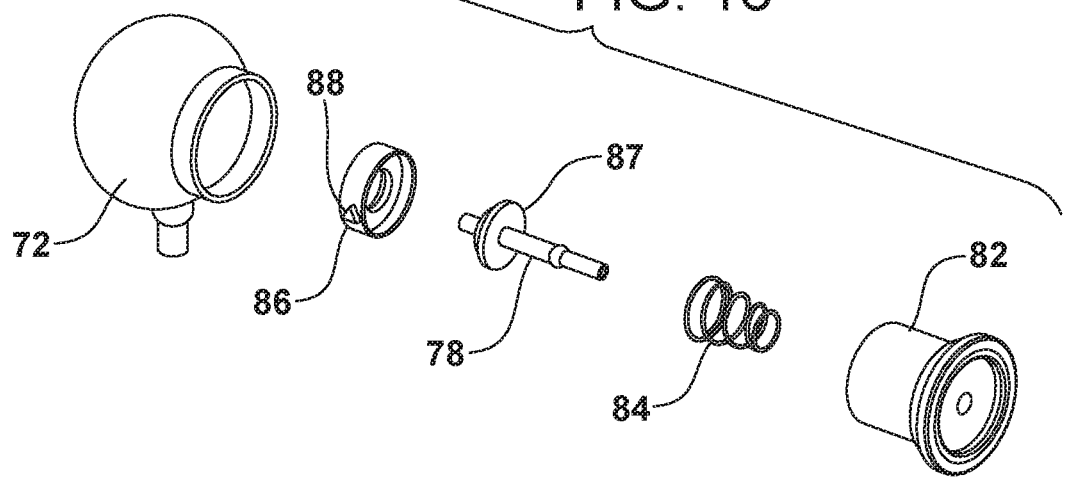
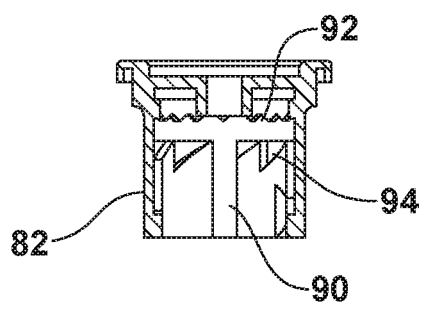
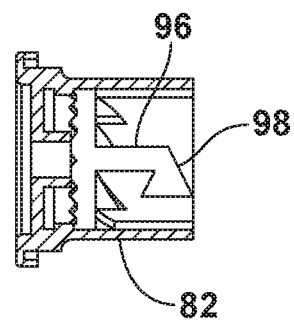

MALE INSERT FOR DRAINING FLUID FROM A PATIENT

TECHNICAL FIELD

This document relates generally to surgical drains, and more specifically to a male insert for draining fluid from a patient.

BACKGROUND

Surgical drains have been in use for many years and are an industry standard. Most modern surgical drains are closed suction drains in which a flexible tube, usually silicone, is placed into the surgical space. Holes or slots in the tube allow fluid egress into the lumen of the tube. The tube extends external to the body via an opening in the skin. Externally, a variable length of tubing is connected to a reservoir. The reservoir collects the body fluid exiting the drain and may also be used to generate suction to aid in fluid evacuation.

While the above surgical drains and methods are simple and time tested, they have several limitations including, for example, difficulty concealing and fitting clothing around the external tube and reservoir, encumbered ambulation and thereby retarded and diminished patient mobility, a need to periodically empty the reservoir, a need to periodically reset the reservoir to keep suction on the system, discomfort for the patient due to traction on the external tubing and reservoir, patient compliance with using the drain appropriately and recording drainage output, pressure felt by physicians to remove drains prematurely because of patient complaints, risk of infection from manipulation of the drain during regular operation and the presence of a static external to internal conduit, the risk of body fluids escaping the reservoir if the reservoir plug comes loose, the exposure of the nurse or caretaker to the patient's body fluid when emptying the reservoir, ease of dislodgment of the drain due to a large external extension and difficulty replacing once removed, designs necessitating continuous evacuation, and single use functionality.

Accordingly, a drain system and related methods are needed which allow for improved patient comfort, compliance, and mobility. Such a drain system would permit multiple functionality including, for example, continuous versus intermittent evacuation, continuous egress of fluid without the need to periodically reset the system suction, and provision of varied treatment modalities including sampling and irrigation. The drain system could also avoid exposure of the caretaker to the patient's body fluids, and accommodate clothing over the drain. In addition, the drain system should afford single use functionality.

SUMMARY OF THE INVENTION

In accordance with the purposes and benefits described herein, a male insert for draining fluid from a patient is provided. The male insert may be broadly described as comprising a housing, a valve stem supported by the housing for pivotal movement about an axis from an extended position allowing insertion into the patient to a retracted position preventing re-insertion into the patient, a tube connected to the valve stem and supported by the housing for rotational movement about the axis, the tube and the valve stem forming a contiguous channel through which the fluid drains, a stop preventing rotational movement of the tube in a first position and allowing rotational movement of the tube in a second position, and a locking tab supported by the housing, the locking tab engaging one of the valve stem and the tube when the valve stem is in the retracted position.

In another possible embodiment, the tube extends outside of the housing.

In still another possible embodiment, the valve stem is at least partially within the housing in the retracted position.

In yet another possible embodiment, the valve stem includes a bulbous portion.

In still yet another possible embodiment, the stop includes a channel for receiving the tube, the channel having a first portion positioned adjacent the tube in the first position and a second portion positioned adjacent the tube in the second position.

In one other possible embodiment, at least a portion of the tube includes a flat outer surface that contacts the first portion of the channel preventing rotational movement of the tube in the first position. In another, the second portion of the channel allows rotational movement of the tube in the second position.

In still another possible embodiment, the stop extends from the housing. In yet another, movement of the stop from the first position to the second position occurs through contact when the valve stem is inserted into the patient.

In another possible embodiment, the stop includes a channel for receiving the tube, the channel having a first portion positioned adjacent the tube in the first position and a second portion positioned adjacent the tube in the second position, at least a portion of the tube includes a flat outer surface that contacts the first portion of the channel preventing rotational movement of the tube in the first position, and the second portion of the channel allows rotational movement of the tube in the second position.

In accordance with another aspect of the invention, a male insert for draining fluid from a patient includes a housing, a valve stem supported by the housing for pivotal movement about an axis from an extended position substantially perpendicular to a side of the housing to a retracted position substantially within the housing, a tube connected to the valve stem and supported by the housing for rotational movement about the axis, the tube and the valve stem forming a contiguous channel through which the fluid drains, and a locking tab supported by the housing, the locking tab engaging one of the valve stem and the tube when the valve stem is in the retracted position preventing further pivotal movement.

In another possible embodiment, the male insert further includes a locking ring encircling the valve stem and extending from within the housing, the locking ring further extending into the housing adjacent the tube preventing rotation of the tube in a first position and allowing rotational movement of the tube in a second position.

In still another possible embodiment, at least a portion of the tube includes a flat outer surface that contacts a surface of the locking ring preventing rotational movement of the tube in the first position.

In yet another possible embodiment, movement of the locking ring from the first position to the second position moves the surface of the locking ring preventing rotation movement of the tube allowing rotational movement of the tube.

In accordance with still another aspect of the invention, a male insert for use with a patient surgical drain system including a male insert for draining fluid from a patient. The patient surgical drain system includes an adapter for insertion into the patient through which the fluid drains through the male insert. The adapter includes first and second valves for controlling movement of the fluid through the adapter and the male insert includes a housing, a valve stem supported by the housing for pivotal movement about an axis from an extended position allowing insertion into the adapter to a retracted position preventing re-insertion into the adapter, a tube connected to the valve stem and supported by the housing for rotational movement about the axis, the tube and the valve stem forming a contiguous channel through which the fluid drains.

In another possible embodiment, a length of the valve stem allows the valve stem to extend through the first and second valves of the adapter when inserted in the extended position.

In one other possible embodiment, the male insert further includes a locking tab, engaging the valve stem when the valve stem is in the retracted position preventing further pivotal movement.

In yet another possible embodiment, the male insert further includes a locking tab engaging the tube when the valve stem is in the retracted position preventing further pivotal movement.

In still another possible embodiment, the male insert further includes a stop preventing rotational movement of the tube in a first position and allowing rotational movement of the tube in a second position.

In still yet another possible embodiment, the valve stem is substantially perpendicular to a side of the housing in the extended position. In another, the valve stem is substantially within the housing in the retracted position.

In another possible embodiment, the valve stem opens the first and second valves when inserted into the adapter allowing the fluid to drain through the valve stem and tube into the attachment.

In one other possible embodiment, the male insert further includes a locking ring encircling the valve stem and extending from within the housing, the locking ring extending into the housing adjacent the tube preventing rotation of the tube in an extended position and allowing rotational movement of the tube in a retracted position.

In another possible embodiment, at least a portion of the tube includes a flat outer surface that contacts a surface of the locking ring preventing rotational movement of the tube in the extended position.

In still another possible embodiment, movement of the locking ring from the extended position to the retracted position moves the surface of the locking ring preventing rotation movement of the tube allowing rotational movement of the tube.

In yet another possible embodiment, the male insert further includes a tab preventing rotational movement of the tube when the valve stem is in the retracted position. In still yet another possible embodiment, the male insert further includes a tab preventing pivotal movement of the valve stem when the valve stem is in the retracted position.

In the following description, there are shown and described several preferred embodiments of the male insert for draining fluid from a patient. As it should be realized, the various male inserts are capable of other, different embodiments and their several details are capable of modification in various, obvious aspects all without departing from the inserts as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the surgical drain system and male insert for draining fluid from a patient and together with the description serve to explain certain principles thereof. In the drawing figures:

FIG. 1 is a perspective view of a surgical drain system showing a drain tube coupled to an attachment via an adapter;

FIG. 2 is a perspective view of the surgical drain system showing a male insert of the attachment withdrawn from the adapter;

FIG. 3 is a partial perspective view of the adapter and drain tube extending therefrom;

FIG. 18 is an exploding perspective view of the retraction mechanism and housing;

FIG. 19 is a cross-sectional plan view of a connector of the retraction mechanism for preventing re-use of an insert;

FIG. 20 is another cross-sectional plan view of the connector of the retraction mechanism for preventing re-use of an insert;

Reference will now be made in detail to the present embodiments of the surgical drain system, examples of which are illustrated in the accompanying drawing figures, wherein like numerals are used to represent like elements.

DETAILED DESCRIPTION

Reference is now made to FIGS. 1 and 2 which illustrate an embodiment of a surgical drain system. The surgical drain system includes an adapter 20 having a flange 22, and drain tube 24 which passes through an incision in the patient's skin. Thus, drain tube 24 is primarily contained internally within the patient's body. An interior face of the flange 22 rests adjacent to the patient's skin surface when the drain tube 24 is inserted into the patient. Suture material may be passed through flange 22 to secure it in place. Alternatively, the flange 22 could contain a hole for suture material to pass through or an anchor post.

In the present described embodiment, the drain tube 24 is integrally formed with the adapter 20 so that they form one continuous, uniform unit. The drain tube 24 includes a distal end, adjacent the flange 22, and a proximal end which extends into the body cavity to be drained. Along a portion of the proximal portion of the drain tube 24, the tube includes a plurality or a multiplicity of holes or channels to allow body fluids to enter a central lumen 26 of the tube. Along a portion of the drain tube 24 near the proximal end, the tube does not include such holes or channels providing a fluid tight tube adjacent the flange.

Figure 4:
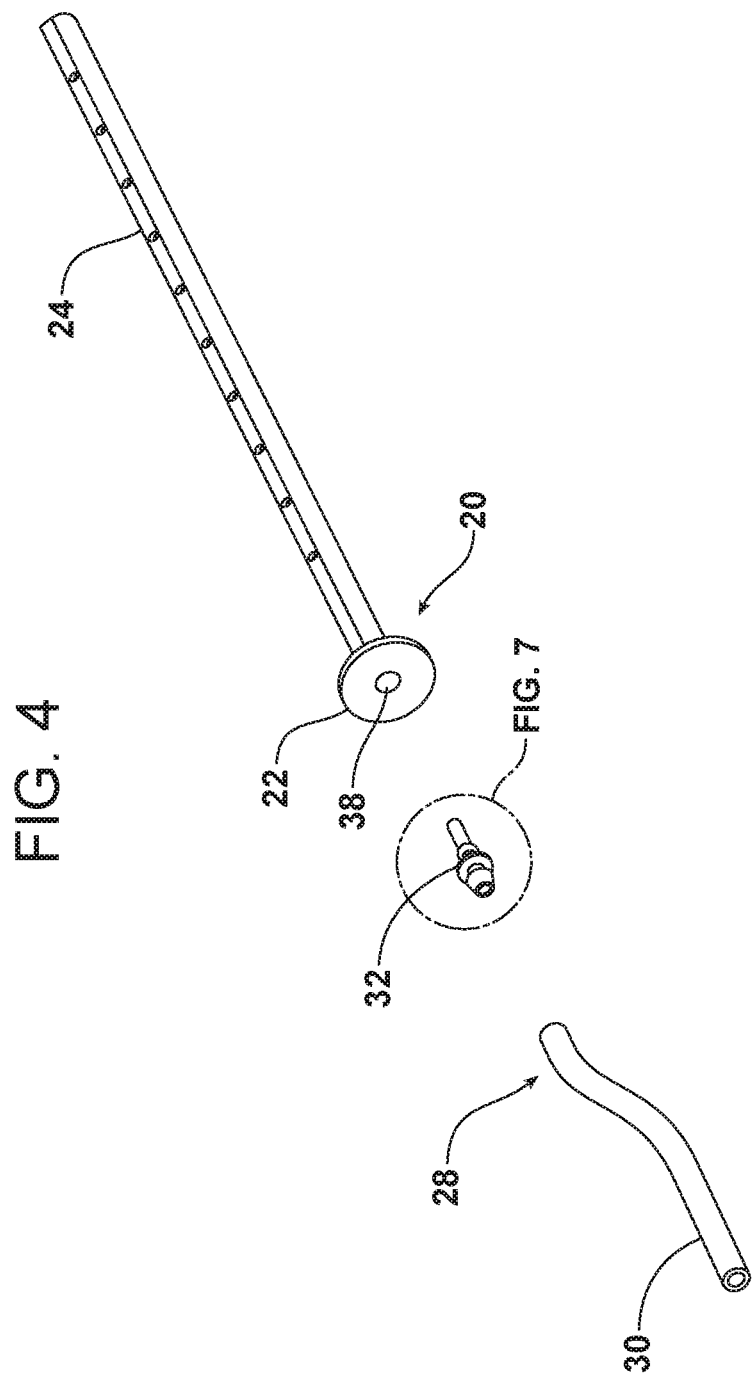
FIG. 4 is an exploding perspective view of the surgical drain system showing an attachment in the form of a tube, a male insert, an adapter, and a drain tube.

As best shown in FIG. 2, a removable attachment 28 (shown attached in FIG. 1) may be detached from the adapter 20. As best shown in FIG. 4, the attachment 28 includes attachment tubing 30, in the described embodiment, and male insert 32 (shown in detail in FIG. 7) having a valve stem 34. As shown, the attachment tubing 30 is connected to the male insert 32 to allow drainage of the fluid. In various embodiments, the attachment tubing 30 may lead to a reservoir or another component of the attachment as described below. Alternatively, the attachment may not include attachment tubing dependent upon what the other component may be. Several such components are described below which can be connected directly to the male insert.

Figure 5:
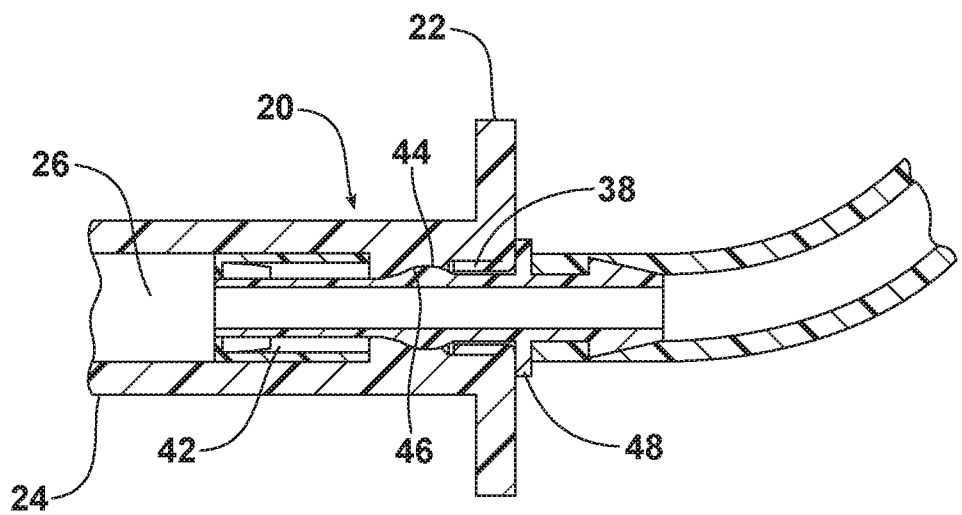
FIG. 5 is a sectional plan view of the adapter, integrally molded drain tube, and the attachment.
Figure 6:
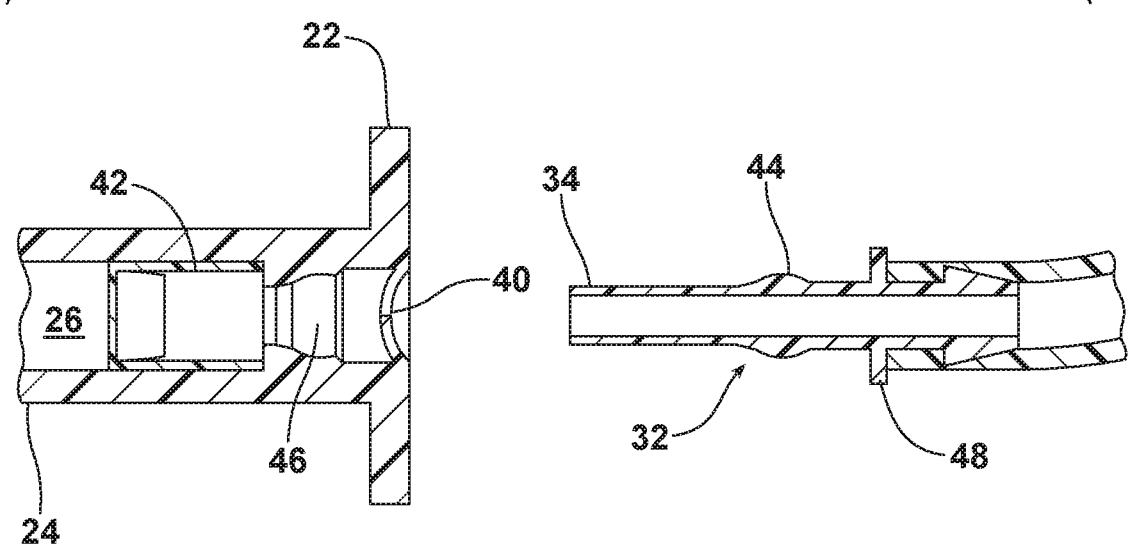
FIG. 6 is an exploding sectional plan view showing the adapter and drain tube and the attachment.

In operation, a user inserts male insert 32 and valve stem 34 into adapter 20. More specifically, the male insert 32 is inserted into an external valve 38 as shown in FIGS. 3 and 5 causing the external valve 38 to be opened which provides access to a port of the adapter 20. As shown in FIG. 6, the external valve 38 may optimally include a shallow central detent 40 to encourage alignment between the external valve and the valve stem 34 of the male insert 32. When the drain tube 24 is inserted, the flange 22 remains external to the body and rests comfortably adjacent the skin surface as described above.

In the described embodiment best shown in FIG. 6, an internal valve 42 is positioned adjacent the distal portion of the drain tube 24. More specifically, the mechanical components of the valve 42 are positioned within the drain tube 24 in the described embodiment. Of course, positioning of the internal valve can vary in different embodiments and depending on how the drain tube and adapter are connected.

The external valve 38 is integrally molded with flange 22 in the described embodiment and is near flush with an outwardly facing surface of the flange. The external valve 38 includes two valve leaflets which are recessed slightly. Again, the valve may be non-integral and formed of other materials and varying types of valves utilized in alternate embodiments.

In the described embodiment, internal valve 42 is integrally model with drain tube 24. External valve 38 and internal valve 42 work together, as shown in FIG. 5, to prevent any leakage from or contamination of the port of adapter 20 and the internal body cavity to which it is connected through drain tube 24. To allow access to the port of adapter 20 and allow fluid flow, the valve stem 34 of the male insert 32 is first inserted through external valve 38 and then through internal valve 42. Internal valve 42 is a duckbill configuration in the described embodiment and may be a separate component which is insert molded or may be integrally molded with drain tube 24. Of course, other valves may be utilized which may or may not be integrally molded.

Figure 7:
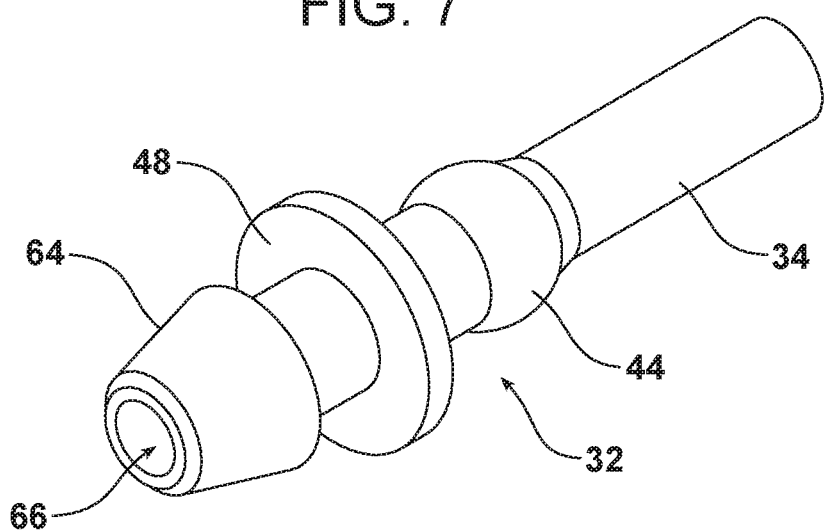
FIG. 7 is a perspective view of the male insert.

As best shown in FIG. 6, a portion 44 of the male insert 32 and a portion 46 of the adapter 20 form an interference fit. An interference fit, also known as a press fit or a friction fit, is a fastening between two parts which is achieved by friction after the parts are pushed together, rather than by any other means of fastening. More specifically as shown in FIG. 7, the portion 44 of the male insert 32 is a substantially bulbous radius that mates and forms the interference fit with the portion 46 of the adapter 20 which is a substantially bulbous cavity. When the male insert 32 is fully seated, the valve stem 34 will stent open internal valve 42, the bulbous radius 44 will be stably positioned within the cavity 46, and a body of the male insert positioned between the bulbous radius 44 and a stop ring 48 will stent open external valve 38. See FIG. 8 for a close-up of the male insert 32.

In this fully seated position, the stop ring 48 forming a part of the male insert 32 abuts or rests flush with the flange 22. Stop ring 48 prevents over insertion of male insert 32 and when the stop ring is flush with the flange 22 serves as a sign that male insert 32 is properly seated. In the described embodiment, stable fluid flow is established between the body cavity, through the drain tube 24, adapter 20, and to the attachment 28. However, with a sufficient amount backward traction on attachment 28 or attachment tubing 30 or male insert 32, the bulbous radius 44 will pop out of or otherwise be dislodged from bulbous cavity 46 and be withdrawn through external valve 38, pulling valve stem 34 out of internal valve 42 and stopping fluid flow without dislodging adapter 20 from the patient's body.

As shown in FIG. 5, the external valve 38 and internal valve 42 of adapter 20 are open thus allowing a central channel for fluid flow. Stop ring 48 prevents over insertion and provides an additional seal to avoid fluid leak. In an alternate embodiment, a twist lock mechanism could be incorporated to provide a stronger connection between male insert 32 and adapter 20.

As shown in FIG. 7, valve stem 34 of male insert 32 extends proximally and the bulbous radius 44 is in a midportion of the male insert. Stop ring 48 extends radially outward. Shown distally is a hose barb 64 to promote secure connection of attachment tube 30 in the described embodiment. A lumen 66 runs the length of male insert 32.

Figure 8:
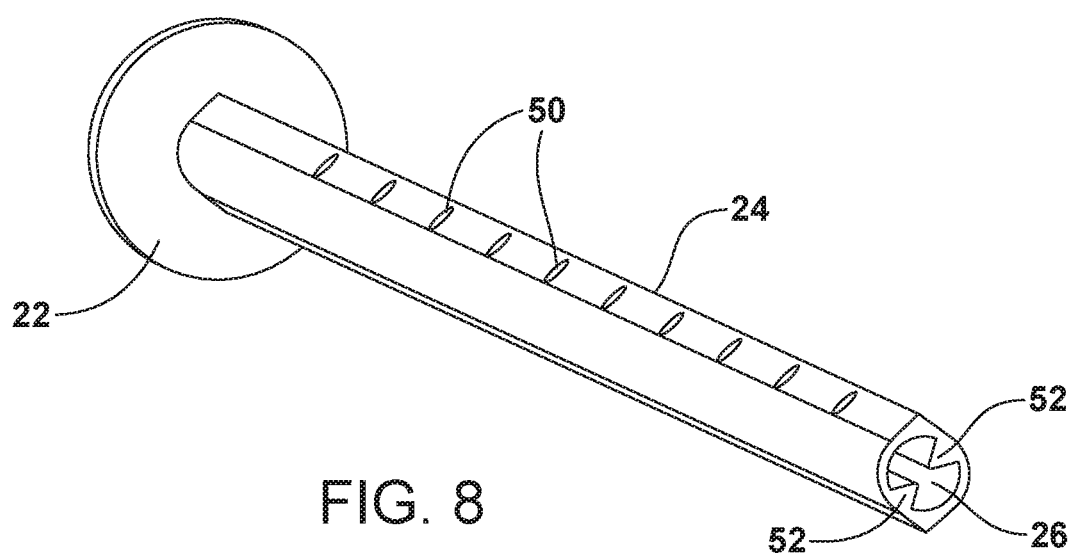
FIG. 8 is a perspective view of a drain tube including a plurality of holes, and ribs extending longitudinally along a lumen of the tube.

As shown in FIG. 8, drain tube 24 is a closed system without any holes adjacent its distal end closest to flange 22 as described above. At its proximal end, drain tube 24 has a multiplicity of drain holes 50. Of note, in the described embodiment, drain tube 24 is elliptically shaped to allow both improved healing of the wound after the drain tube is removed and to provide an enhanced seal through a linear incision. This design also adds rigidity to the system preventing inadvertent collapse of the drain tube 24 by surrounding tissue, and allows improved fluid flow through drain holes 50 by preventing surrounding tissue from obstructing the holes. In an alternate embodiment, additional rigidity may be added to drain tube 24 by incorporating drain tube ribs 52 that run longitudinally along a central lumen 26.

Figure 9:
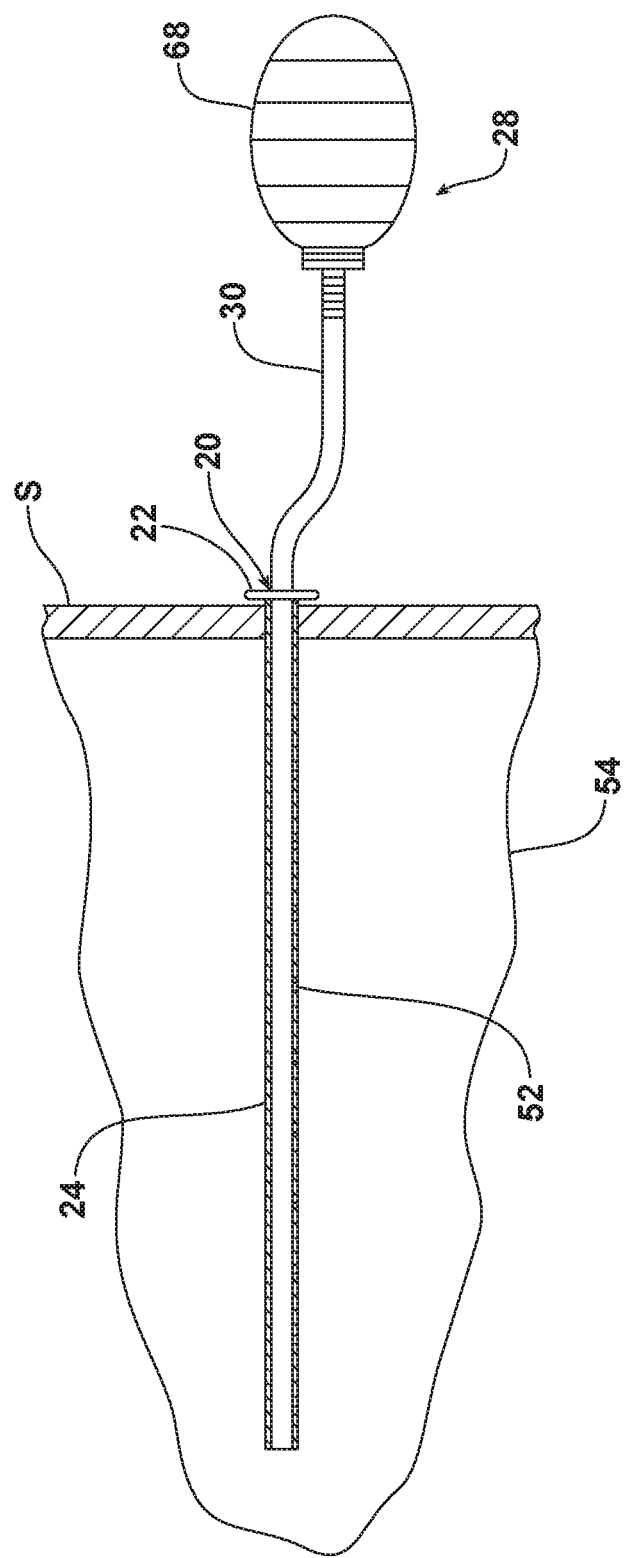
FIG. 9 is a perspective view of a surgical drain system showing a drain tube extending through an incision in a patient's skin, an adapter, and an attachment in the form of a bulb reservoir.

In accordance with the method of use of the present invention as illustrated in FIG. 9, adapter 20 is positioned on the skin surface with drain tube 24 inserted through the skin (S). Drain tube 24 extends internally into the body cavity to be drained. Multiplicities of drain inlet holes 52 are located at the proximal end of drain tube 24 to allow fluid egress into the lumen. The user may cut off a portion of the proximal end of drain tube 24 as desired for the specific application. Alternatively, channels may be placed in the proximal end of drain tube 24 to encourage fluid egress out of the body cavity and into the lumen. External to the skin, the proximal aspect of attachment 28 is shown here configured as a bulb reservoir 68 connected to adapter 20. In this embodiment, attachment tubing 30 extends from male insert 32 to an industry standard bulb reservoir 68.

Figure 10:
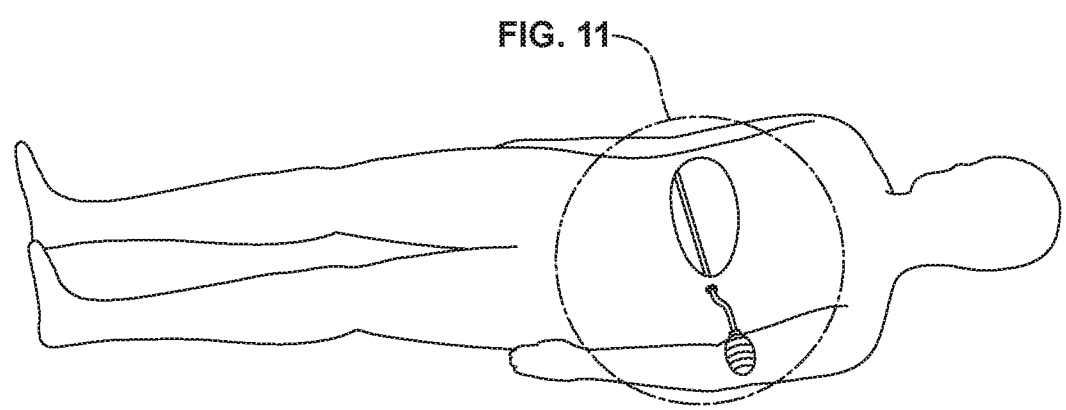
FIG. 10 is a perspective view of the full patient with the surgical drain system shown in FIG. 9 positioned therein.
Figure 11:
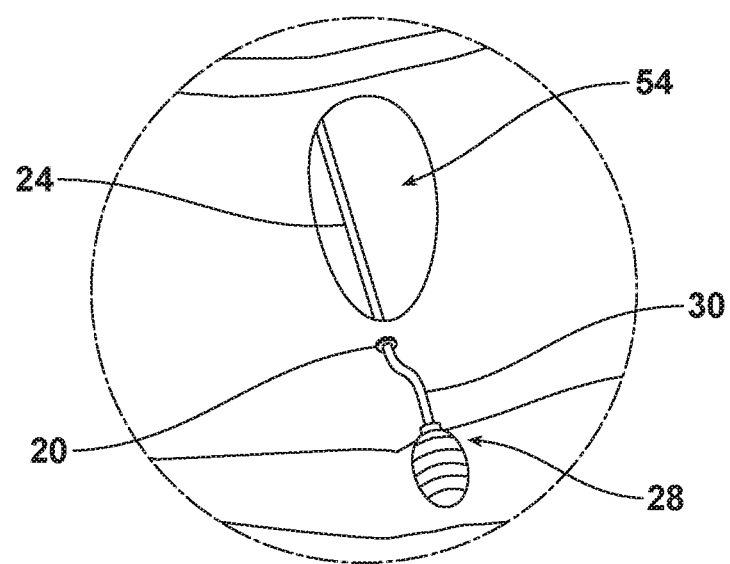
FIG. 11 is a partial perspective view of FIG. 10 showing a close-up view of the drain tube positioned within the patient.

Placement of the drain tube 24 is perhaps best shown in FIGS. 10 and 11 wherein the drainage system is shown as utilized in a patient. Drain tube 24 resides inside the body cavity or surgical space 54. The adapter 20 is external and secured to the skin surface by adhesive, suture, or combinations thereof. A removable attachment 28 is connected to the adapter 20 for receiving the fluid drained from the patient. As shown, the attachment 28 includes a bulbous reservoir. This attachment may be left connected to the adapter 20 for as long as desired, or may be intermittently removed and/or replaced so long as sterility is maintained. With this attachment in place, the system functions identically to a current industry standard drain. In this embodiment, fluid egress is encouraged by vacuum pressure as the collapsed bulb expands. The standard bulbs contain a valve for removal of fluid and air from the bulb. The valve is then re-capped with the bulb collapsed generating suction.

Of course, the attachment 28 may take many forms as will be generally described below. Primarily the removable attachments are single use disposable devices each of which includes a male insert 32 to connect into the adapter 20. Various attachments are provided that accommodate the multiplicity of function inherent in the system. Several exemplary attachments are provided in the subsequent description but additional extensions may be developed with time and need. Although not described in each exemplary attachment, a valve such as a check valve, may be utilized to prevent leakage of drained fluid collected within the attachments. Such a valve may be positioned distal to the valve stem 34 to prevent leakage after disconnection of the attachment 28.

Figure 12:
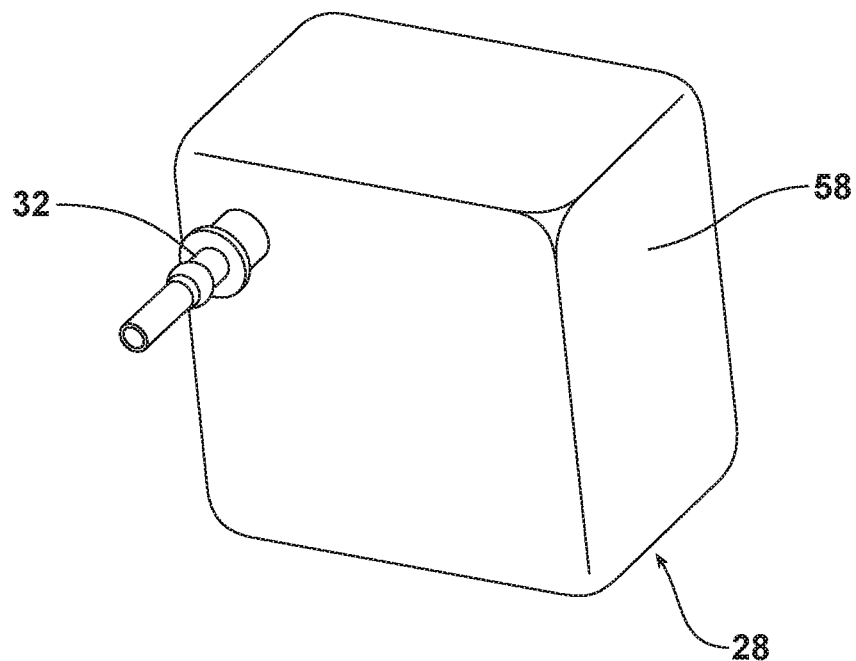
FIG. 12 is a perspective view of an attachment in the form of a reservoir with an osmotic material positioned therein for absorbing fluid.

As shown in FIG. 12, the attachment 28 may include a male insert 32 attached to a chamber 58. In the described embodiment, the chamber 58 includes an absorbent or superabsorbent material therein and the chamber itself is flexible. The chamber 58 may be of various shapes, and preferably is designed to conform to the natural curves of the body. Thus, flexible chamber 58 may be cylindrical, rectangular as shown, or curved depending on the planned anatomic area of use. Note that male insert 32 is positioned in a corner, generally offset a distance equal to the adapter 20, so that it can move and seek a comfortable position when the patient moves. Flexible chamber 58 is sealed with the exception of the opening through male insert 32. A one-way check valve (e.g., a duck bill valve as is known in the art) could also be incorporated to prevent fluid egress out of the chamber after the super absorbent material has been saturated. In the present described embodiment, flexible chamber 58 is transparent or semi-transparent to allow the user to visually evaluate the superabsorbent material. Alternatively, a length of flexible tubing which may or may not contain an osmotically active material could extend between male insert 32 and flexible chamber 58.

The presently described embodiment of the chamber 58 provides a colorimetric indication of when the super-absorbent material has been fully saturated. The capacity of each reservoir is indicated on its housing. Determination of the amount of fluid egress from the drain is important to determine the time for drain removal. An alternate embodiment may provide a dry weight for the reservoir. The user could calculate the amount of fluid which has been absorbed by weighing the reservoir upon removal.

The reservoir may be supplied in multiple different capacities and shapes, including an expandable housing. Thus, early in the postoperative phase, when drainage is copious, a large capacity reservoir would be utilized. Later, when drainage has tapered off and the patient is becoming more mobile, a smaller anatomically contoured reservoir may be utilized. Fluid egress from the surgical space is thus provided by osmotic action upon the fluid column extending outward to the absorbent material in the reservoir 58.

Figure 13:
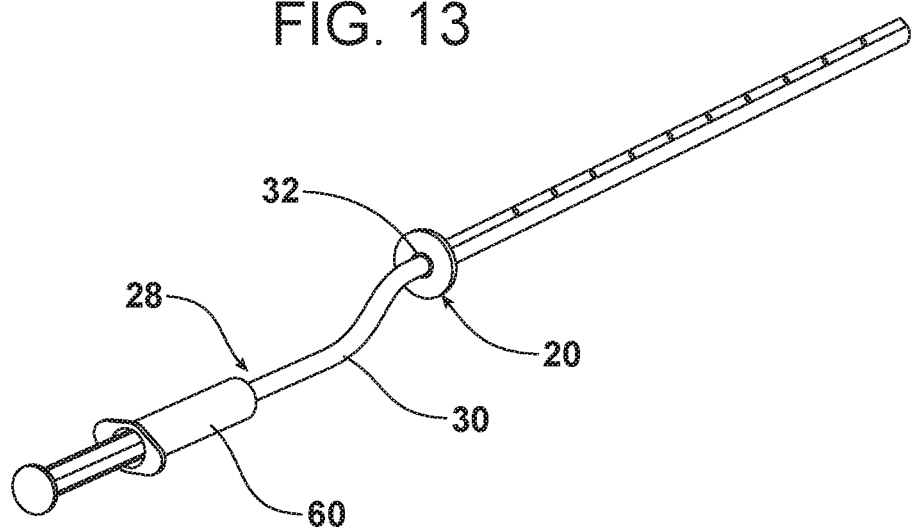
FIG. 13 is a perspective view of a surgical drain system showing an attachment in the form of a syringe, a male insert, an adapter, and a drain tube.

Another attachment shown in FIG. 13, includes a male insert 32, inserted into adapter 20, with an integrally molded Luer or slip-on fitting on an opposing distal end to connect to a syringe 60. Alternatively, an intervening length of an attachment tube 30 may extend between the male insert 32 and Leur or slip fitting to allow easier connection of syringe 60. The user would attach the syringe 60 to the Leur or slip-on fitting and then insert the male insert 32 into the adapter 20. The user could then draw out body fluids from the surgical space by means of vacuum pressure with the syringe 60. Alternatively, the user could instill fluids or medications contained within the attached syringe 60.

Another attachment might include only a removable and/or replaceable cap (not shown) to seal off the adapter 20. The cap would further minimize the risk of fluid entering the surgical site in addition to the barrier already provided by the external and internal valves 38, 42. The cap may be made of rigid or flexible material. It attaches to the adapter 20 utilizing a fitting or by means of an adhesive, a slide fitting, a clip, a screw fitting, or a magnetic coupling. Preferably, the cap is a single use disposable component which is supplied sterilely. Alternatively, the cap may be fixed to the adapter 20. In one embodiment, the cap is a single use disposable self-adherent membrane which completely covers the adapter 20 with or without a portion of the surrounding skin. The cap also serves to minimize the risk of fluid escape from adapter 20. As a further alternative embodiment, the removable cap could be designed to allow perforation of it with a needle to permit fluid flow.

Another attachment includes a wall suction adapter which consists proximally of a male insert 32 connected to a hollow bore flexible tubing 30 and distally to a fitting compatible with standard hospital suction tubing. Commonly when drains are initially placed, fluid output is high, thus this system provides a convenient method to evacuate and quantitate the fluid. A further benefit is that continuously applied suction may help to collapse or close the body cavity in which the proximal end of the drain resides.

An alternate embodiment could also include a method to generate suction either by expansion of a partially collapsed reservoir or a spring loaded mechanism. The osmotic reservoir, for example, has the same male insert 32 directly attached or molded to it to connect with the adapter 20. Alternately, there may be a tubing 30 running between the reservoir 58 and the male insert 32. A fluid conductive medium could also be contained in the lumen of the drain tube 24 inside the patient's body to serve as a wick to enhance flow of fluid along an osmotic pathway. Alternatively, a superabsorbent material could be placed inside the drain tube 24 and changed periodically to soak up body fluids without requiring the external reservoir. Of note, in this latter embodiment, the superabsorbent material would have to be provided sterilely.

As noted above, the attachment may be utilized for irrigation. Such an attachment 28 would provide a route for installation of irrigation fluid and drugs. The irrigation attachment 28 includes the male insert 32 affixed to a hollow tubing 30 which distally includes an attachment point for a syringe, IV tubing, three way valve or other medical connector familiar to those skilled in the art. This provides access for irrigation of the body cavity into which the proximal aspect of the drain tube 24 resides to decrease bacterial contamination. Drugs such as antibiotics, chemotherapeutics or sclerosants could also be instilled via this conduit. Fluid egress could occur sequentially through the same flow pathway, or a second complete drain system setup could provide for fluid removal.

Another attachment 28 includes a surgical access fitting (not shown). This attachment would enter sterilely through the adapter 20 into the patient's body and would serve as a conduit through which treatment could be administered. Through this access point, the inner body cavity could be inspected under direct or video assisted visualization. A biopsy may be performed or fluid collected to assist with diagnosing possible medical conditions. Treatments may also be performed through this access point including directed application of suction and/or debridement. In one embodiment, a port that is similar to a laparoscopic port would connect to the adapter 20 and could be used as a conduit for the introduction of laparoscopic instruments. Subsequently the attachment could be removed leaving the adapter 20 intact. As with the other attachments, a male insert 32 provides the conduit through which the instruments pass.

In still another attachment 28, the attachment includes an automated evacuation system. This attachment provides for automated evacuation of the drain powered by any of several means including but not limited to compressed gas, electrically driven pump, Archimedes screw or a vacuum reservoir. The automated evacuation system could include electrical timing control as well as an automated monitoring of fluid output or precisely regulating outward fluid flow by way of a second valve or a mechanical pump. On its distal end, this attachment could have a connection point for a reservoir.

Figure 15:
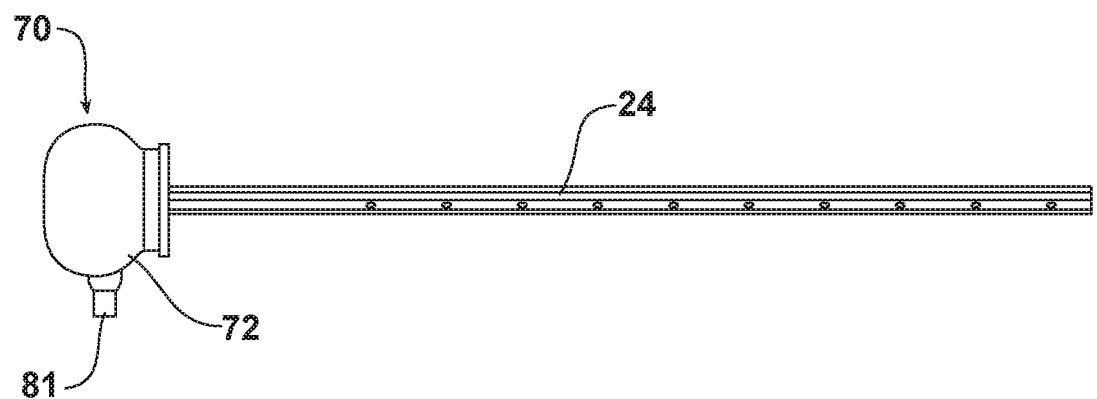
FIG. 15 is a side plan view of a surgical drain system showing an attachment including a retraction mechanism inserted into an adapter.

In certain alternate embodiments of the invention, an insert 70 which actively prevents more than a single use may be utilized in place of insert 32. Broadly speaking, the insert 70 works generally like a ball point pen retraction/extension mechanism except the mechanism is limited to a single cycle. As shown in FIG. 15, the insert 70 attaches to the drain tube 24 and may include a housing 72 wherein a retraction mechanism 74 generally resides. The housing 72 may be a connector bulb made of silicone rubber, rubber, or another elastomeric material and may further include a connector 81 for connecting various attachments, drain tubes, etc. thereto. In the described embodiment, the retraction mechanism 74 automatically prevents subsequent use of the insert 70 when triggered. In other words, the retraction mechanism 74 ensures that the insert 70 cannot be re-inserted into the drain tube 24 after it is removed.

Figure 16:
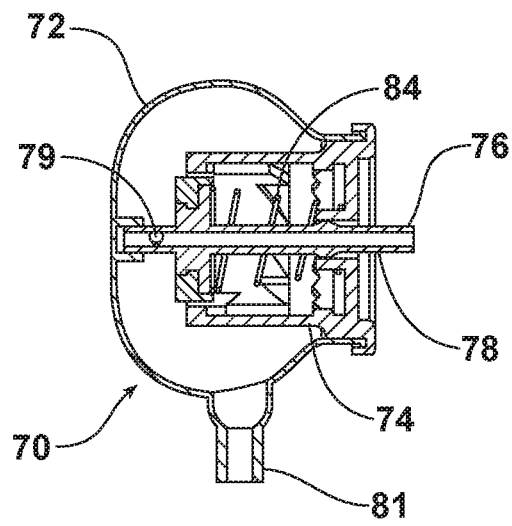
FIG. 16 is a cross sectional plan view of the retraction mechanism in a retracted position within a housing.
Figure 17:
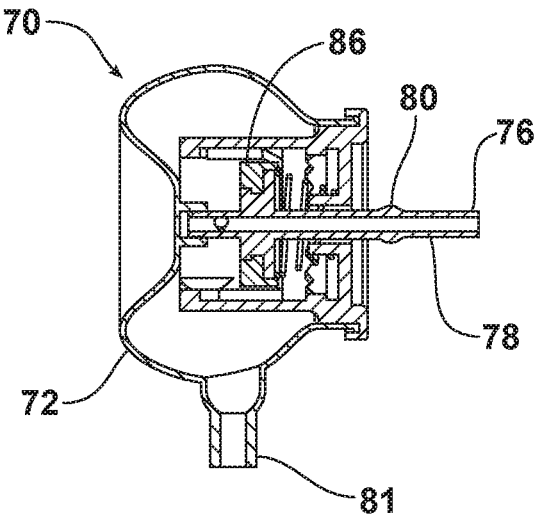
FIG. 17 is a cross sectional plan view of the retraction mechanism in an extended position within the housing.

FIGS. 16 and 17 provide cross-sectional views of the retraction mechanism 74 positioned within the housing 72. The housing 72 is shown in a retracted position in FIG. 16 and an extended position in FIG. 17. As shown in FIG. 16, a proximal tip 76 of a valve stem 78 of the insert 70 extends from the housing 72. In operation, the user aligns the valve stem tip 76 with the adapter 20. Once aligned, the valve stem tip 76 may be inserted into the external valve 38 as previously described. Depressing the housing 72 as shown in FIG. 17, extends the valve stem 78 into the external valve 38 causing the external valve to be opened which provides access to the port of the adapter 20 in much the same manner the earlier described insert 32 behaved. The valve stem 78 includes an aperture 79 allowing fluid to outlet into the housing 72 and out the drain tube 24. As shown in FIG. 17, the insert 70 even includes a bulbous radius 80 which forms a portion of an interference fit used for fastening the insert 70 and the adapter 20 together during use. The bulbous radius 80 mates with the cavity 46 and the interference fit performs as described above.

Upon either planned or inadvertent removal of the insert 70 from the port, the insert is retracted and the retraction mechanism 74 locks the insert in a retracted position preventing re-insertion. Although not shown, a check valve may also be included to prevent flow out of the insert 70 when retracted. The user could also retract the insert 70 for removal by pushing in slightly on the housing 72 and the retraction mechanism 74 and then releasing same thereby triggering retraction of the insert.

As shown in exploded view in FIG. 18, the retraction mechanism 74 positioned within connector housing 72 includes a connector 82, a spring 84, the valve stem 78 and a rotating lock ring 86. In the described embodiment, the lock ring 86 includes at least one tooth or tab 88 protruding from an outer surface of the lock ring. The lock ring 86 is bifurcated and snaps together over the valve stem 78. More specifically, flanges 87 of the valve stem 78 hold the rotating lock ring 86 in position during operation.

The connector 82 is shown in cross-sectional views in FIGS. 19 and 20. As shown in FIG. 19, the connector 82 includes an insertion track 90 for rotating the lock ring 86, advancement spurs or teeth 92, and internal ratchets 94 for holding the lock ring 86 in the extended position. As shown in FIG. 20, the connector 82 further includes a track 96 and a final track 98 to hold the lock ring 86 captive and to prevent re-extension of the valve stem 78.

During insertion, the user applies pressure using a thumb, or otherwise, to an exterior of housing 72. The pressure forces the insert 70 and the valve stem 78 to advance from the initial retracted position shown in FIG. 16 to the extended position shown in FIG. 17. Extension of the valve stem 78 causes a rotation of the lock ring 86 within the connector 82 and the internal ratchets 94 hold the lock ring in the extended position throughout use. To remove the insert 70 and the valve stem 78, the user applies additional pressure to the exterior of the housing 72 in order to advance the valve stem an additional partial step. Once advanced, the lock ring 86 is sufficiently further rotated to release from the internal ratchets 94 holding the lock ring in the extended position. A rearward traction is placed on the housing 72 causing the housing to move distally in relation to the insert 70 and the valve stem 78. This forces the lock ring 86 to interact with gear teeth 92 causing a radial motion of the valve stem 78 into alignment with slots of the connector 82 and triggering a sliding motion of the valve stem distally into the housing 72. The pre-loaded spring 84 provides a sufficient amount of force to drive valve stem 78 back into the housing 72. If the user attempts to re-insert the valve stem 78, the lock ring 86 is further rotated into a fixed, locked position which prevents extension of the valve stem.

Figure 21:
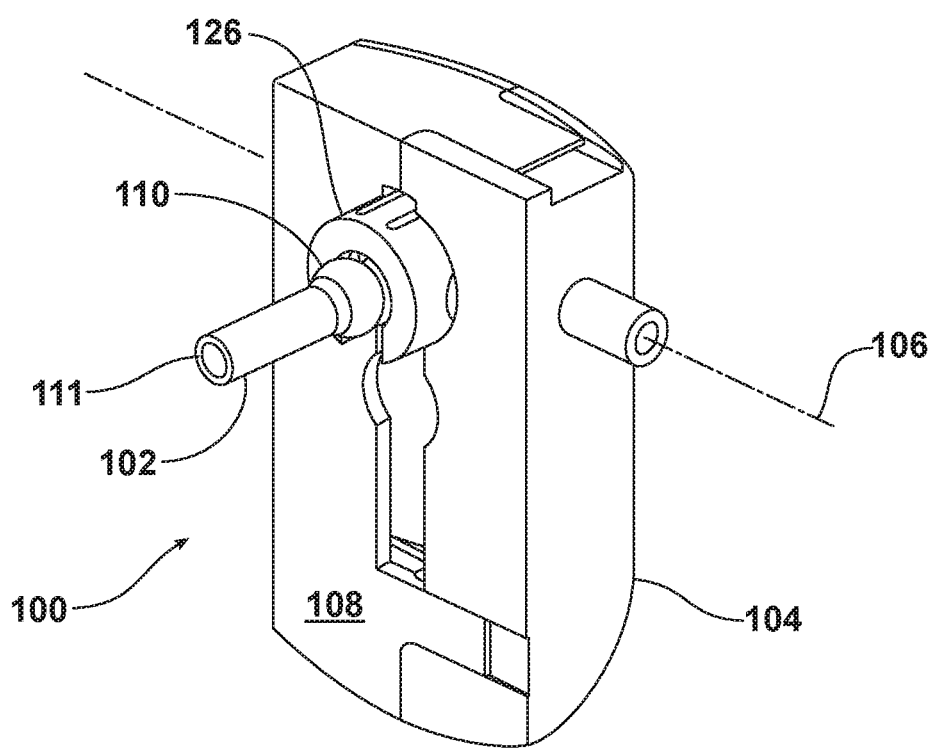
FIG. 21 is a perspective view of an alternate embodiment of a male insert for draining fluid from a patient.

In still another alternate embodiment of the invention, a male insert 100 that designed to prevent more than a single use may be utilized in place of insert 32. As shown in FIG. 21, the insert 100 includes a valve stem 102 supported by a housing 104 for pivotal movement about an axis 106. The valve stem 102 is shown in an extended position allowing insertion into a patient. In the described embodiment, the valve stem 102 is substantially perpendicular to a side 108 of the housing 104 in the extended position. The valve stem 102 may be positioned in any orientation relative the housing 104 in other embodiments so long as the position allows the valve stem to be inserted into the patient through an adapter or otherwise (e.g., the valve stem may extend upward out a top of the housing, downward out a bottom of the housing, or any position between 0 and 180 degrees so long as the position allows the valve stem to be inserted into the patient).

As described in detail above, the valve stem 102 may be inserted into an adapter (e.g., adapter 20) having a flange 22 and drain tube 24 which passes through an incision in the patient's skin. In the described embodiment, the valve stem 102 performs as described above with regard to the adapter 20, first and second valves 38, 42, and bulbous cavity 44, and includes a bulbous portion 110. In this embodiment, however, the valve stem 102 pivots from the extended position allowing insertion to a retracted position preventing insertion into the adapter/patient. In the retracted position, a distal end portion 111 of the valve stem 102 is at least partially within the housing 104. In other embodiments, the valve stem 102 may be completely within the housing 104 or sufficiently close to the housing to prevent re-use, i.e., re-insertion.

Figure 22:
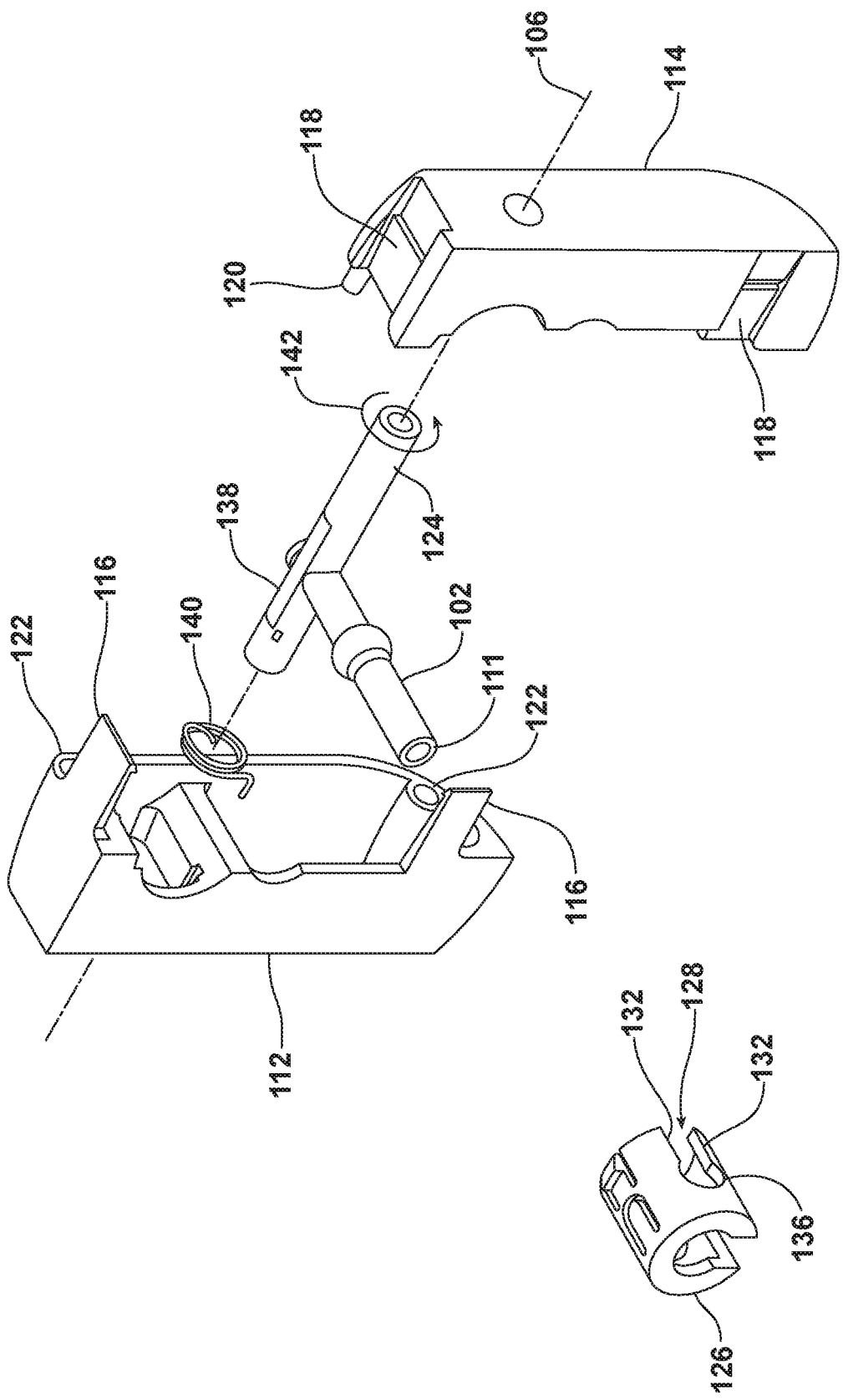
FIG. 22 is an exploded perspective view of the male insert.

As shown in FIG. 22, the described housing 104 includes first and second halves 112, 114 which are joined together by snap tabs 116. The snap tabs 116 latch onto corresponding receivers 118 positioned on the opposing half. Alignment pins 120 are provided to ensure that the first and second halves 112, 114 are properly aligned when joined together. Corresponding apertures 122 are provided on the opposing halves. While the present embodiment employs two alignment pins and corresponding apertures, more or fewer may be utilized in other embodiments.

As further shown, a tube 124 is connected to the valve stem 102 and supported by the housing 104 for rotational movement about the axis 106 as shown by action arrow 142. The tube 124 and the valve stem 102 form a contiguous channel through which the fluid drains. In the described embodiment, the tube 124 extends outside of the housing 104 in one direction as shown in FIG. 21. In alternate embodiments, the tube 124 may extend outside of the housing 104 in both directions, may terminate in a receiver supported by the housing, or otherwise, for connecting to an attachment (e.g., attachment 28 including any of the attachments described above), or the tube may extend beyond the housing 104 serving the same purpose as the attachment tubing 32 described above.

Figure 23:
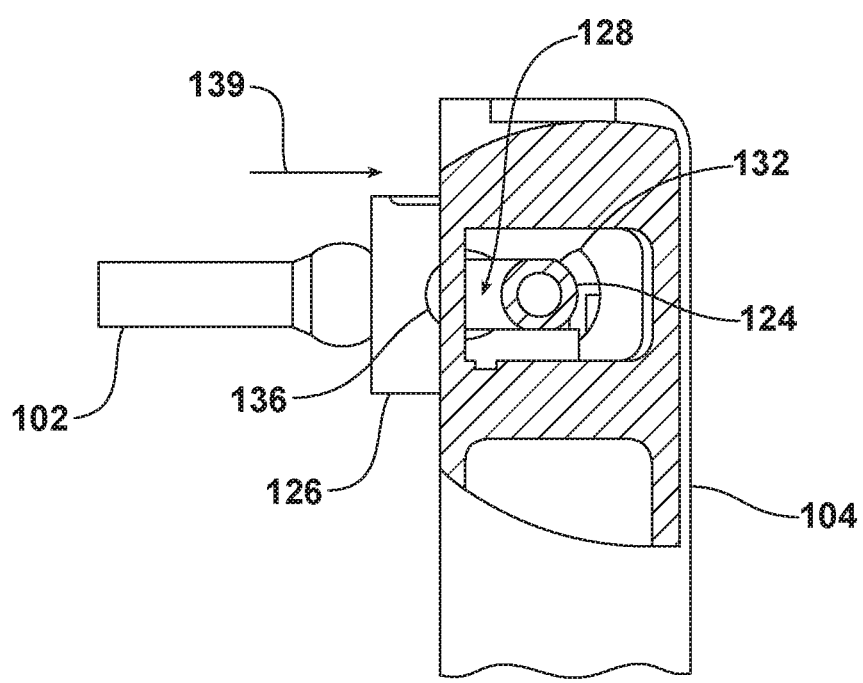
FIG. 23 is a partial cross-sectional plan view of the male insert showing a stop preventing rotational movement of a tube.

Returning to FIG. 21, a stop 126 prevents rotational movement of the tube 124 in a first position and allows for rotational movement of the tube in a second position. The stop 126 is also referred to as a locking ring given that the described embodiment encircles the valve stem 102. The stop 126 is shown in the first position, i.e., extending from within the housing 104, in FIG. 23. As shown, the stop 126 further extends into the housing 104 and defines a channel 128 formed therein for receiving the tube 124. The channel 128 includes a first portion positioned adjacent the tube 124 in the first position. The first portion includes essentially straight sides 132. The channel 128 also includes a second portion positioned adjacent the tube in the second position. In the second position, the stop 126 is moved rearward, i.e., to the right in FIG. 23, such that the second portion, including rounded sides 136, is adjacent the tube 124.

In use, the straight sides 132 of the first portion contact the tube 124 and prevent it from rotating when the stop 126 is in the first position. As best shown in FIG. 22, at least a portion of the tube 124 includes a flat outer surface 138 that contacts the first portion of the channel 128 preventing rotational movement. The tube 124 may include upper and lower flat outer surfaces that contact the straight sides 132 of the first portion of the channel 128 formed in the stop 126. The valve stem 102 is inserted into the adapter 20 and extends through and opens the first and second valves 38, 42 allowing the fluid to be drained from the patient. During insertion of the valve stem 102, the stop 126 will contact the flange 22 of adapter 20 causing the stop to move from the first position to the second position in a direction indicated by action arrow 139. In other words, through contact with the flange 22, the stop 126 is moved into the housing 104 allowing the tube 124 to align with the second portion of channel 128. The rounded sides 136 of the second portion allow the tube 124 to rotate about the axis 106. In other embodiments, the stop may be hand-operated and may be positioned elsewhere on the housing.

Figure 24:
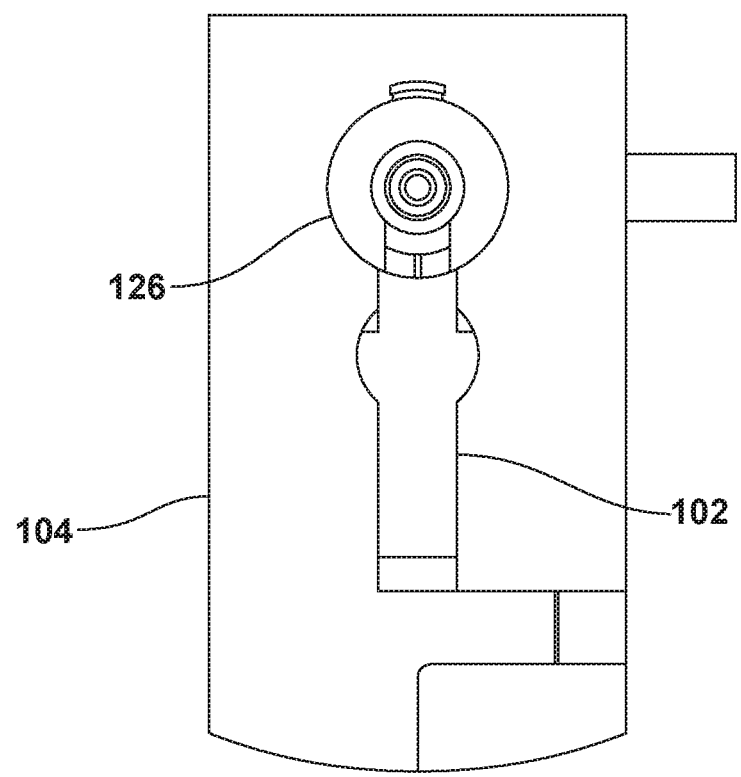
FIG. 24 is a front plan view of the male insert showing a valve stem in a retracted position.

In the described embodiment, a spring 140 supported within the housing 104 provides a rotational force on the tube 124. As the valve stem 102 is withdrawn from the adapter 20 and with the stop 126 in the second position allowing for rotation, the force of the spring 140 rotates the tube 124 (as shown by action arrow 142 in FIG. 22) moving the valve stem from the extended position to the retracted position. As shown in FIG. 24, the valve stem 102 is entirely within the housing 104 in the retracted position in the described embodiment. As indicated above, however, the retracted position may or may not be within the housing 104.

Figure 25:
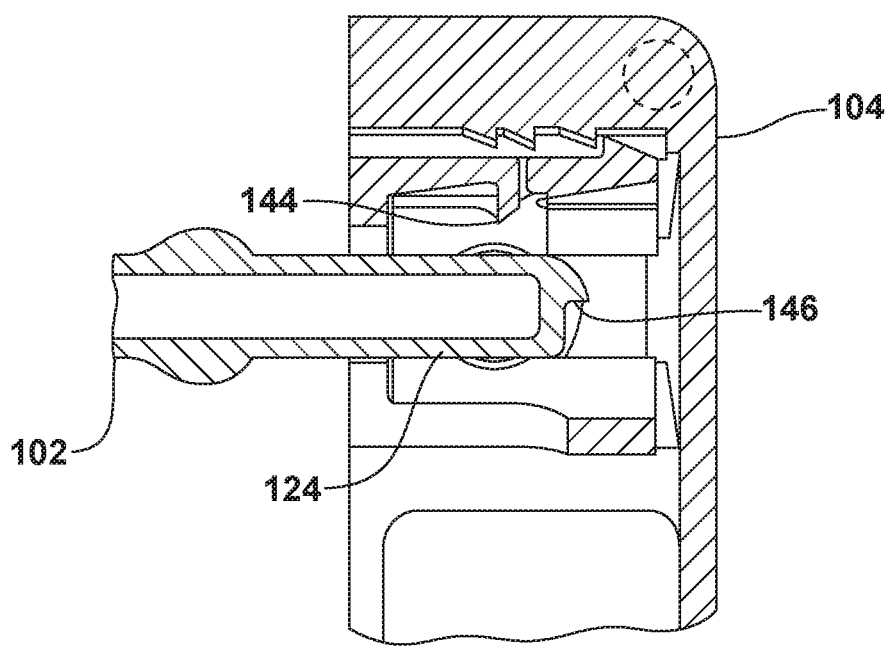
FIG. 25 is a partial cross-sectional plan view of the male insert showing the valve stem in an extended position and a locking tab.
Figure 26:
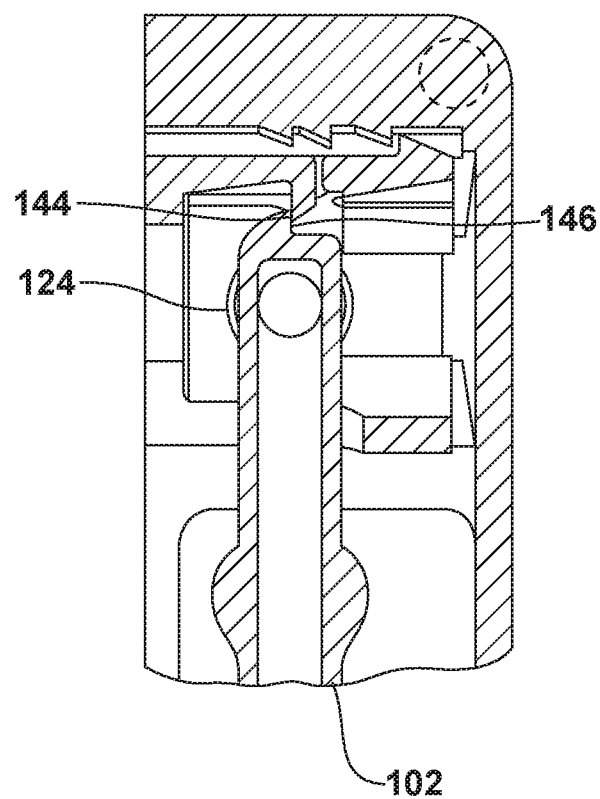
FIG. 26 is a partial cross-sectional plan view of the male insert showing the locking tab engaging a rearward portion of the valve stem preventing pivotal movement of the valve stem from the retracted position.
Figure 27:
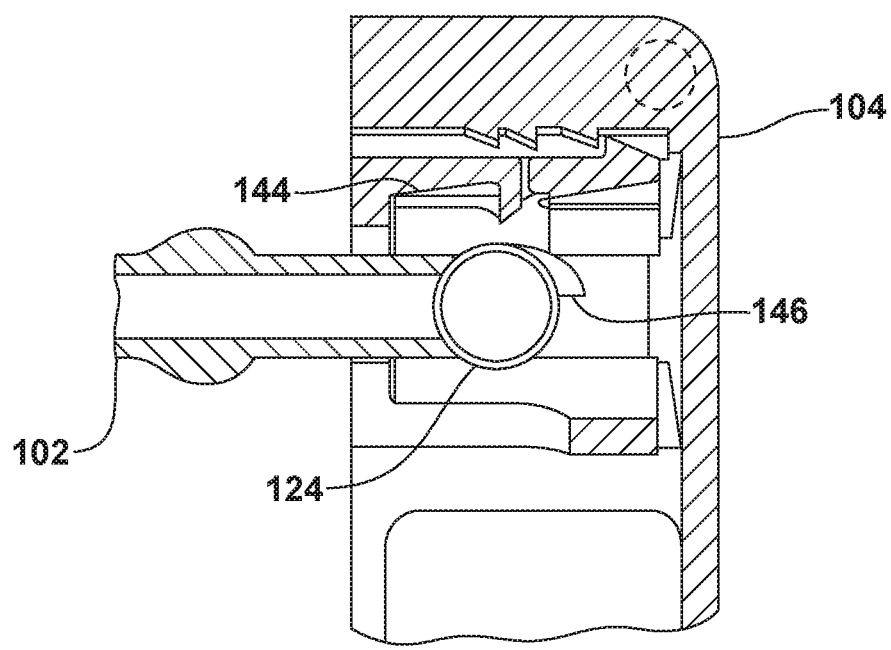
FIG. 27 is a partial cross-sectional plan view of an alternate embodiment of a male insert showing the locking tab engaging a rearward portion of the tube.

In accordance with the single-use feature of the male insert 100, a locking tab 144 extends into a path of the pivoting valve stem 102 as shown in FIG. 25. More specifically, a notch is formed in a rearward portion of the valve stem 102 creating a side wall 146. As the valve stem 102 pivots from the extended position to the retracted position, the rearward portion rotates about the axis 106. At the retracted position as shown in FIG. 26, the locking tab 144 engages the side wall 146 preventing the valve stem 102 from further pivoting movement. Of course, the locking tab may extend into the path of the pivoting valve stem 102 or the tube 124 from essentially any direction and a holding surface (e.g., the side wall 146) may be formed on any portion of the valve stem or tube. For instance, the locket tab 144 may engage the tube 124 as shown in FIG. 27.

In summary, numerous benefits result from providing a surgical drain system that allows for improved patient comfort, compliance, and mobility. The surgical drain system permits multiple functionality including, for example, continuous versus intermittent evacuation, continuous egress of fluid without the need to periodically reset the system suction, and provision of varied treatment modalities including sampling and irrigation. The drain system also avoids exposure of the caretaker to the patient's body fluids, accommodates clothing over the drain, and limits use of the male insert.

Figure 14:
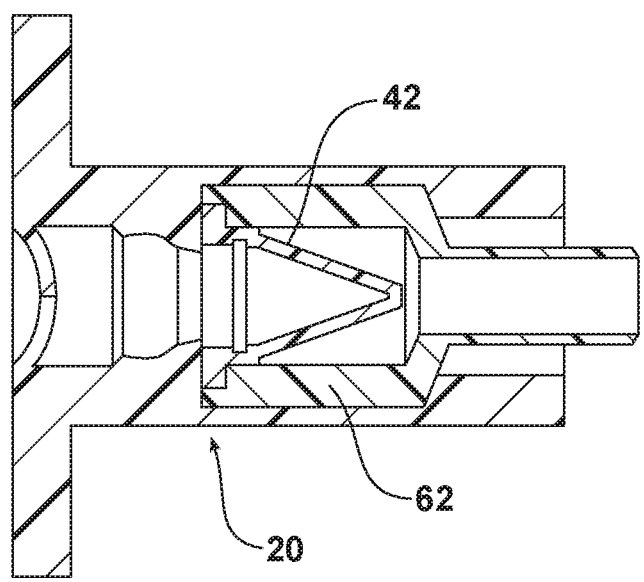
FIG. 14 is a sectional plan view of an alternate embodiment of an adapter including a stabilizing insert.

The foregoing has been presented for purposes of illustration and description. It is not intended to be exhaustive or to limit the embodiments to the precise form disclosed. Obvious modifications and variations are possible in light of the above teachings. As shown in FIG. 14, for example, an alternate adapter 20 may include a stabilizing insert 62 supporting internal valve 42. The stabilizing insert 62 may be made of a rigid material including polymer, metal, or metal alloy to provide an antimicrobial effect, and other components may be selected that have antimicrobial properties. All such modifications and variations are within the scope of the appended claims when interpreted in accordance with the breadth to which they are fairly, legally and equitably entitled.

What is claimed:

1. A male insert for use with a patient surgical drain system, comprising:
    a housing;
    a valve stem supported by said housing for pivotal movement from an extended position allowing insertion of the valve stem into the patient to a retracted position; and
    a tube connected to the valve stem and supported by the housing for rotational movement about a longitudinal axis of the tube, the tube and the valve stem forming a contiguous channel through which the fluid drains.

2. The male insert for use with a patient surgical drain system of claim 1, further comprising a locking ring encircling the valve stem and extending from within the housing, the locking ring extending into the housing adjacent the tube preventing rotation of the tube in a first position and allowing rotational movement of the tube in a second position.

3. The male insert for use with a patient surgical drain system of claim 2, wherein an outer surface of the tube contacts a surface of the locking ring preventing rotational movement of the tube in at least the first position.

4. The male insert for use with a patient surgical drain system of claim 3, wherein movement of the locking ring from the first position to the second position moves the surface of the locking ring preventing rotational movement of the tube allowing rotational movement of the tube.

5. The male insert for use with a patient surgical drain system of claim 1, further comprising a locking tab, the locking tab engaging the valve stem when the valve stem is in the retracted position preventing further pivotal movement.

6. The male insert for use with a patient surgical drain system of claim 1, further comprising a locking tab, the locking tab engaging the tube when the valve stem is in the retracted position preventing further pivotal movement.

7. The male insert for use with a patient surgical drain system of claim 1, further comprising a stop preventing rotational movement of the tube in a first position and allowing rotational movement of the tube in a second position.

8. The male insert for use with a patient surgical drain system of claim 1, wherein the valve stem is substantially perpendicular to a side of the housing in the extended position.

9. The male insert for use with a patient surgical drain system of claim 1, wherein the valve stem is substantially within the housing in the retracted position.

10. The male insert for use with a patient surgical drain system of claim 1, further comprising a tab preventing rotational movement of the tube when the valve stem is in the retracted position.

11. The male insert for use with a patient surgical drain system of claim 1, further comprising a tab preventing pivotal movement of the valve stem when the valve stem is in the retracted position.

12. A male insert for draining fluid from a patient, comprising:
    a housing;
    a valve stem supported by said housing for pivotal movement about an axis from an extended position allowing insertion into the patient to a retracted position preventing re-insertion into the patient;
    a tube connected to said valve stem and supported by said housing for rotational movement about the axis, said tube and said valve stem forming a contiguous channel through which the fluid drains;
    a stop preventing rotational movement of said tube in a first position and allowing rotational movement of said tube in a second position; and
    a locking tab supported within said housing, said locking tab engaging one of said valve stem and said tube when said valve stem is in the retracted position.

13. The male insert for draining fluid from a patient of claim 12, wherein said stop includes a channel for receiving said tube, said channel having a first portion positioned adjacent said tube in the first position and a second portion positioned adjacent said tube in the second position.

14. The male insert for draining fluid from a patient of claim 13, wherein at least a portion of said tube includes a flat outer surface that contacts said first portion of said channel preventing rotational movement of said tube in the first position.

15. The male insert for draining fluid from a patient of claim 14, wherein said second portion of said channel allows rotational movement of said tube in the second position.

16. The male insert for draining fluid from a patient of claim 12, wherein said stop extends from said housing.

17. The male insert for draining fluid from a patient of claim 16, wherein movement of said stop from the first position to the second position occurs through contact when said valve stem is inserted into the patient.

18. The male insert for draining fluid from a patient of claim 16, wherein said stop includes a channel for receiving said tube, said channel having a first portion positioned adjacent said tube in the first position and a second portion positioned adjacent said tube in the second position, at least a portion of said tube includes a flat outer surface that contacts said first portion of said channel preventing rotational movement of said tube in the first position, and said second portion of said channel allows rotational movement of said tube in the second position.

19. The male insert for draining fluid from a patient of claim 12, wherein said tube extends outside of said housing.

20. The male insert for draining fluid from a patient of claim 12, wherein said valve stem is at least partially within said housing in the retracted position.

21. The male insert for draining fluid from a patient of claim 12, wherein said valve stem includes a bulbous portion.

22. A male insert for draining fluid from a patient, comprising:
    a housing;
    a valve stem supported by said housing for pivotal movement about an axis from an extended position substantially perpendicular to a side of said housing to a retracted position substantially within said housing;

a tube connected to said valve stem and supported by said housing for rotational movement about the axis, said tube and said valve stem forming a contiguous channel through which the fluid drains; and a locking tab supported by said housing, said locking tab engaging one of said valve stem and said tube when said valve stem is in the retracted position preventing further pivotal movement, wherein the axis extends longitudinally within the tube.

23. The male insert for draining fluid from a patient of claim 22, further comprising a locking ring encircling said valve stem and extending from within said housing, said locking ring further extending into said housing adjacent said tube preventing rotation of said tube in a first position and allowing rotational movement of said tube in a second position.

24. The male insert for draining fluid from a patient of claim 23, wherein at least a portion of said tube includes a flat outer surface that contacts a surface of said locking ring preventing rotational movement of said tube in the first position.

25. The male insert for draining fluid from a patient of claim 24, wherein movement of said locking ring from the first position to the second position moves the surface of the locking ring preventing rotation movement of said tube allowing rotational movement of said tube.

26. The male insert for draining fluid from a patient of claim 22, wherein said valve stem includes a bulbous portion.

27. The male insert for draining fluid from a patient of claim 22, wherein said tube extends outside of said housing.

* * * * *

UNITED STATES PATENT AND TRADEMARK OFFICE
CERTIFICATE OF CORRECTION

PATENT NO. : 10,898,697 B2  
APPLICATION NO. : 15/725614  
DATED : January 26, 2021  
INVENTOR(S) : Ben Marsico et al.

Page 1 of 1

It is certified that error appears in the above-identified patent and that said Letters Patent is hereby corrected as shown below:

In the Claims

Column 14, Claim 17, Line 43 - please delete "through contact"

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*